Figure 1:
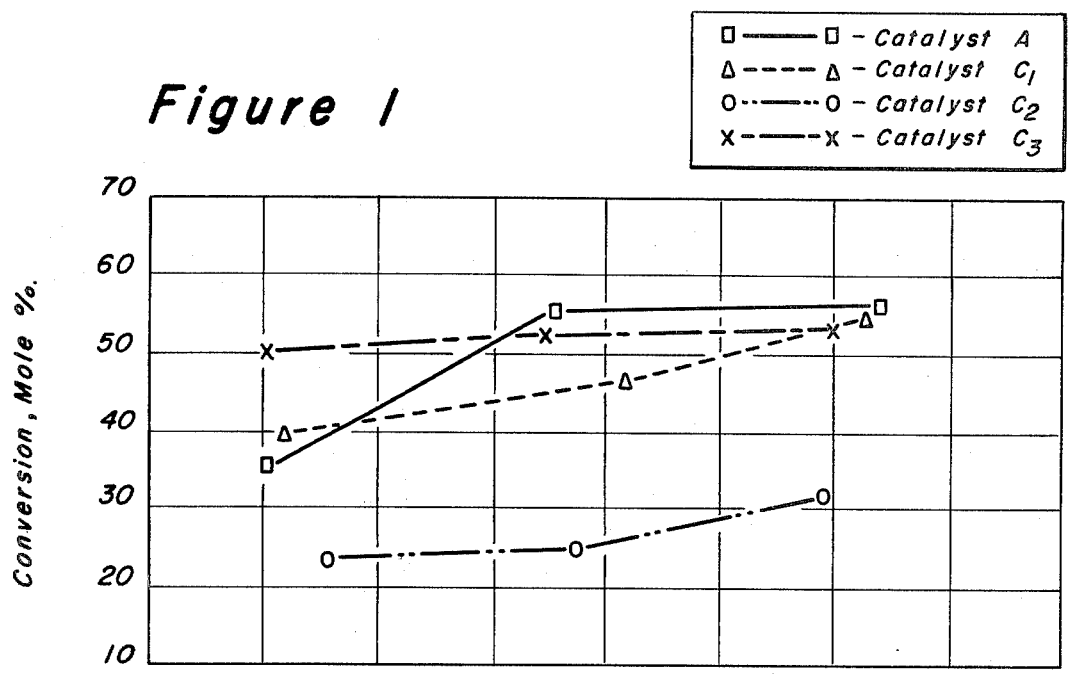

United States Patent [19]

Imai

[11] 4,180,690
[45] Dec. 25, 1979

[54] OXYDEHYDROGENATION OF ALKYLAROMATIC HYDROCARBONS AND CATALYTIC COMPOSITE THEREFOR

[75] Inventor: Tamotsu Imai, Mount Prospect, Ill.

[73] Assignee: UOP Inc., Des Plaines, Ill.

[21] Appl. No.: 862,071

[22] Filed: Dec. 19, 1977

[51] Int. Cl.² ............................................. C07C 15/00
[52] U.S. Cl. ................................................... 585/443
[58] Field of Search ................. 260/669 R; 252/455 R

[56] References Cited

U.S. PATENT DOCUMENTS

| 3,502,737 | 3/1970 | Ghublikian | 260/669 R |
| 3,941,854 | 3/1976 | Franz et al. | 260/669 R |
| 4,009,218 | 2/1977 | Uitti | 260/669 R |
| 4,052,338 | 10/1977 | Riesser | 260/669 R |

FOREIGN PATENT DOCUMENTS 596616   1/1948   United Kingdom ................ 260/669 R Primary Examiner—Delbert E. Gantz
Assistant Examiner—Joseph A. Boska
Attorney, Agent, or Firm—James R. Hoatson, Jr.; Thomas K. McBride; William H. Page, II

[57] ABSTRACT

Dehydrogenatable alkylaromatic hydrocarbons are oxydehydrogenated by contacting them at oxydehydrogenation conditions with specified amounts of steam and oxygen in the presence of an active and selective catalytic composite comprising a combination of catalytically effective amounts of cobalt oxide, chromium oxide, alumina and magnesium oxide with a silica carrier material. A specific example of the active and selective catalytic composite disclosed herein for use in oxydehydrogenation of alkylaromatic hydrocarbons is a combination of cobalt oxide, chromium oxide, alumina and magnesium oxide with a silica carrier material in amounts sufficient to result in a mole ratio of chromium oxide to cobalt oxide of about 0.2:1 to about 2:1, of alumina to cobalt oxide of about 0.05:1 to about 0.5:1 and of magnesium oxide to cobalt oxide of about 0.05:1 to about 0.5:1. A key feature involves using this catalytic composite in the oxydehydrogenation of dehydrogenatable alkylaromatic hydrocarbons at an inlet reactor temperature greater than 470° C.

9 Claims, 3 Drawing Figures

OXYDEHYDROGENATION OF ALKYLAROMATIC HYDROCARBONS AND CATALYTIC COMPOSITE THEREFOR

The subject of the present invention is broadly an improved method for oxydehydrogenating an aromatic hydrocarbon having at least one dehydrogenatable alkyl group substituent to produce an alkenyl-substituted aromatic hydrocarbon containing the same number of carbon atoms but fewer hydrogen atoms. In another narrower aspect, the present invention involves a method of oxydehydrogenating ethylbenzene in order to selectively produce styrene in high yield without the high utility cost, yield limitations and heat transfer limitations of the prior art adiabatic steam-dehydrogenation process. In yet another aspect, the present invention relates to a novel active and selective multimetallic catalyst composite comprising a combination of catalytically effective amounts of cobalt oxide, chromium oxide, alumina and magnesium oxide with a silica carrier material, which composite has been found to have highly beneficial properties of activity, selectivity and overall yield when it is employed in the oxydehydrogenation of aromatic hydrocarbons having at least one dehydrogenatable alkyl group substituent to produce an alkenyl-substituted aromatic hydrocarbon; for example, the oxydehydrogenation of ethylbenzene to produce styrene, of isopropylbenzene to produce alpha-methylstyrene and of diethylbenzene to produce divinylbenzene.

The dehydrogenation of dehydrogenatable alkylaromatic hydrocarbons is an important commercial process because of the substantial existing demand for alkenyl-substituted aromatic hydrocarbons for use in the manufacture of a wide variety of common chemical products such as detergents, plastics, synthetic rubbers, pharmaceutical products, ion exchange resins, and various other commercial products well known to those skilled in the art. One example of this commercial demand is in manufacture of styrene from ethylbenzene wherein the resulting product finds substantial commercial utility in such products as polystyrene, rubber-modified polystyrene, styrene-butadiene copolymer, styrene acrylonitrile copolymer and acrylonitrilebutadiene-styrene terpolymer. These styrene-based polymer systems are widely used in such commercial products such as housewares, appliances, automobiles, toys, heat insulating material, emulsifying agents, paint, coatings for cloth and paper, ion exchange resins, and the like commercial materials. In addition, styrene is used in the manufacture of styrenebutadiene rubber which finds wide utility as a high performance synthetic rubber. Another example of the demand for alkenylaromatic hydrocarbons is associated with the production of alpha-methylstyrene from isopropylbenzene (cumene); their product is widely used in polymer formations and in the manufacture of drying oils, ion exchange resins, paints, waxes, adhesives, plastics and the like material. A third area of demand for these alkenyl-aromatic hydrocarbons is in the production of divinylbenzenes from mixtures of m- and p-diethylbenzenes. The resulting divinylbenzenes find wide utility for use in the manufacture of resins, plastics, styrenebutadiene rubber, and ion exchange resins. Still another product of substantial commercial interest in this area is the vinyltoluene which is manufactured from ethyltoluene by steam dehydrogenation and finds commercial application in paints, varnishes and various polyester formulations.

Responsive to this demand for these alkenyl-substituted aromatic hydrocarbons, the art has developed a number of alternative methods to produce them in commercial quantities. The most widely practiced method is steam dehydrogenation in the presence of an appropriate dehydrogenation catalyst at low pressures and high temperatures. The catalyst used in this type of process is typically one that consists of a major amount of iron oxide, a minor amount of an alkaline material such as potassium oxide or carbonate and a catalytically effective amount of chromium oxide. Another type of catalyst that is used in this type of process is a calcium-nickel-phosphate catalyst system. Yet another catalyst which has been suggested for use in this type of dehydrogenation service is a zinc oxide-magnesium oxide-alumina catalyst system. The straight steam dehydrogenation process suffers from a number of handicaps or impediments in that the process is highly endothermic, it is equilibrium limited, and is plagued by substantial side reactions leading to undesired products such as benzene, toluene and various high molecular weight tars and polymers. In order to circumvent some of these limitations of the traditional steam dehydrogenation process, particularly the requirement of the process for tremendous quantities of heat, the art has in a number of places suggested the addition of oxygen to the reaction environment in order to induce the in situ exothermic reaction of oxygen with hydrogen produced during the dehydrogenation reaction thereby shifting this equilibrium controlled reaction towards the product side and greatly diminishing or eliminating the requirement for external heat due to the strongly exothermic reaction of the added oxygen with the hydrogen produced in the desired dehydrogenation reaction. This idea of using oxygen to act as a hydrogen scavenger or getter and provide an internal source of heat for the main reaction, is disclosed in numerous places including U.S. Pat. Nos. 2,945,900; 3,502,737 and 3,247,273. The oxygen-based processes that have been disclosed in the prior art have unfortunately not been completely satisfactory in that the presence of oxygen in the reaction environment has caused many additional problems due to the tendency of the oxygen reactant to react not only with the as produced hydrogen but also with the alkylaromatic hydrocarbon feed and the alkenyl-aromatic product, thereby adversely affecting the selectivity of the overall dehydrogenation reaction for the desired hydrocarbon product. Another problem that has been caused by the presence of oxygen in the reaction environment is detrimental interaction with the catalyst in certain cases, causing a marked decrease in preferential characteristics of same such as activity and selectivity. The detrimental effect of oxygen on a conventional iron oxide dehydrogenation catalyst is disclosed and discussed in U.S. Pat. No. 2,945,900 at column 4, lines 35 through 54. These adverse effects of adding oxygen to an alkylaromatic dehydrogenation process are also discussed in U.S. Pat. No. 3,502,737 wherein it is indicated that the art has tried to overcome these difficulties by turning to other catalyst systems and/or moving towards a fluidized reactor system design. Consequently, the problem addressed by the present invention is, broadly stated, the use of oxygen in an alkylaromatic dehydrogenation process in order to maximize the benefits, outlined above, associated therewith and to minimize the detriments hereinabove discussed.

Before getting to the merits of the present invention, it is convenient to define certain of the terms used in this area of the art in order to quantify the phenomena observed in a steam dehydrogenation process with various types of catalysts. As is the case with most catalytic procedures, the principal measure of effectiveness for this steam dehydrogenation method involves the ability to perform its intended function with minimum interference from side reactions, such as coke formation, dealkylation, combustion of hydrocarbons instead of hydrogen, and the formation of various other byproducts by various polymerization and/or condensation reactions. The analytical terms used in the art to broadly measure how well a particular catalyst system performs its intended functions in a specific hydrocarbon conversion reaction such as steam dehydrogenation of ethylbenzene to produce styrene are activity, selectivity and stability. For purposes of the present discussion, these terms are generally defined for a given reactant as follows: (1) activity is the measure of the catalyst ability to convert the hydrocarbon reactant into products at a specified severity level where severity level means the specific reaction conditions used—that is, the temperature, pressure, contact time, and the presence of diluents such as steam which contribute directly or indirectly to the overall rate at which the reaction occurs; (2) selectivity typically refers to the amount of desired product or products obtained relative to the amount of reactant charged or converted (when the basis of the selectivity number is the amount of reactant converted then the resulting number is referred to herein as product-selectivity and when the basis of the selectivity number is the amount of reactant charged, the resulting parameter is called herein yield-selectivity); (3) stability refers to the rate of change with time of the activity and selectivity parameters—obviously the smaller rate of change implying the more stable catalyst system. More specifically, in an ethylbenzene dehydrogenation process, activity commonly refers to the amount of conversion that takes place for a given ethylbenzene charge rate at a specified severity level and is typically measured on the basis of disappearance of ethylbenzene and expressed in mole percent of ethylbenzene charged; products-selectivity is typically measured by the amount of styrene obtained at the particular activity or severity level relative to the amount of ethylbenzene disappearing, expressed on a mole percent basis; yield-selectivity is, on the other hand, commonly stated as the moles of styrene produced divided by the moles of ethylbenzene charged, expressed on a mole percent basis; and stability is typically equated to the rate of change with time of activity is measured by disappearance of ethylbenzene and of product-or yield-selectivity change as measured by the amount of styrene produced, expressed on the appropriate basis. Against this background the problem addressed by the present invention might be, accordingly, restated as the development of a more active and selective catalyst system for steam dehydrogenation of an alkylaromatic hydrocarbon in the presence of oxygen.

I have now found a multimetallic catalytic composite which possesses improved activity, selectivity and stability characteristics when it is employed in an oxydehydrogenation process designed to produce an alkenylaromatic hydrocarbon from a charge stock containing a dehydrogenatable alkylaromatic hydrocarbon. I have determined in particular that the use of a multimetallic catalyst, comprising a combination of catalytically effective amounts of cobalt oxide, chromium oxide, magnesium oxide, alumina with a porous silica carrier material, can enable the performance of an oxydehydrogenation process to be substantially improved--particularly, in the area of yield-selectivity at moderate temperatures. The novel catalytic composite of the present invention is especially useful in the oxydehydrogenation of ethylbenzene to produce styrene with minimization of side reactions such as dealkylation, oxidation of hydrocarbons, coke-formation, and polymerization. The subject matter of the present invention is based on my finding that a combination of alumina and magnesium oxide can be used, under the circumstances disclosed herein, to beneficially interact with and promote a silica-based catalyst system using a combination of chromium oxide and cobalt oxide to perform the desired dehydrogenation reaction.

It is accordingly one object of the present invention to provide a novel method for the oxydehydrogenation of dehydrogenatable alkylaromatic hydrocarbons utilizing a multimetallic catalytic composite comprising a combination of catalytically effective amounts of cobalt oxide, chromium oxide, magnesium oxide and alumina with a porous silica carrier material. A second object is to provide a novel activated catalytic composite having a superior performance characteristic when it is utilized in a oxydehydrogenation process for making alkylaromatic hydrocarbons at a temperature of above about 470° C. Another object is to provide an improved method for the oxydehydrogenation of dehydrogenatable alkylaromatic hydrocarbons to produce alkenyl-substituted aromatic hydrocarbons which method minimizes undesired side reactions such as dealkylation, uncontrolled combustion of feed or product hydrocarbons, coke-formation and polymerization reactions.

In brief summary, one embodiment of the present invention involves a novel catalytic composite comprising a combination of cobalt oxide, chromium oxide, alumina and magnesium oxide with a silica carrier material in amounts sufficient to result in a mole ratio of chromium oxide to cobalt oxide of 0.2:1 to about 2:1, of alumina to cobalt oxide of about 0.05:1 to about 0.5:1 and of magnesium oxide to cobalt oxide of about 0.05:1 to about 0.5:1.

A second embodiment relates to an oxydehydrogenation method wherein an aromatic input hydrocarbon having at least one dehydrogenatable alkyl group substituent is contacted with steam and oxygen in the presence of the catalyst defined in the first embodiment at oxydehydrogenation conditions including an inlet reactor temperature greater than 470° C. to produce an alkenyl-substituted aromatic product hydrocarbon.

A more specific embodiment of the present invention involves a method for oxydehydrogenating ethylbenzene to produce styrene comprising contacting ethylbenzene, steam and oxygen with the catalyst defined in the first embodiment at oxydehydrogenation conditions including an inlet reactor temperature greater than 470° C.

Other objects and embodiments of the present invention involves specific details regarding the essential and preferred ingredients of the novel catalytic composite, preferred amounts of these ingredients, methods for preparing the unique multimetallic catalytic composite disclosed herein, suitable dehydrogenatable alkylaromatic hydrocarbons that can be charged to the method of the present invention, specific oxydehydrogenation conditions for use in the disclosed reaction, and the like particulars which are hereinafter given in the following detailed discussion of each of these facets of the present invention.

The dehydrogenatable hydrocarbons that is subjected to the method of the present invention is broadly defined as an aromatic hydrocarbon having at least one dehydrogenatable alkyl group substituent. In general, the alkyl groups or group substituted on this hydrocarbon may contain from about 2 to about 20 or more carbon atoms and should further contain at least one hydrogen atom attached to each of at least two adjacent carbon atoms. This input aromatic hydrocarbon is converted by the instant method principally to alkenyl-substituted aromatic product hydrocarbon having the same carbon configuration as the input hydrocarbon but possessing a monoolefinic function. More specifically, in accordance with the present invention, ethylbenzene is converted to styrene, diethylbenzene is converted to divinylbenzene, cumene is converted to alpha-methylstyrene, and ethyltoluene is converted to vinyltoluene. Other alkyl-substituted aromatic hydrocarbons which can be treated in accordance with the method of the present invention include: (1) alkylbenzenes such as p-,diisopropylbenzene, 1,3-diethyl-5-methylbenzene, p-ethylcumene, 1,2,4,-triethylbenzene, p-cymene, and the like alkylbenzenes; (2) alkyl-substituted polynuclear aromatic hydrocarbons such as 1-ethylnaphthalene, 1-isopropylnaphthalene, 2,6-diethylnaphthalene, 2,6-diisopropylnaphthalene, 7-isopropyl-1-methylphenanthrene and the like alkyl-substituted polynuclear aromatic hydrocarbon; and (3) the chloroethylbenzene such as p-chloroethylbenzene, 2,3-dichloroethylbenzene and the like chloro and alkyl-substituted aromatic hydrocarbons. The preferred charge stock is ordinarily a stream which is rich in ethylbenzene.

The multimetallic catalyst used in the present invention comprises a porous silica carrier material or support having combined therewith catalytically effective amounts of cobalt oxide, chromium oxide, alumina and magnesium oxide. The silica carrier material may be prepared in any suitable manner and may be synthetically prepared or naturally occurring. Whatever type of silica is employed, it may be activated prior to use by one or more treatments including drying, calcination, steaming and the like. This silica material may be used in a form known as silica gel of commerce, porous silica gel and the like materials. This silica carrier material may be prepared by adding a suitable acidic reagent, such as sulfuric acid, to a water glass solution in order to cause a base-acid inversion thereby producing a thermally setting acid silica sol which can be worked up into spherical particles of porous silica gel by methods well known by those skilled in the art. The silica carrier material may be formed into any desired shape such as spheres, pills, pellets, powder, cakes, extrudates, sodler, tablets and the like and utilized in any desired size, with symmetrical spheres or pellets of 1/50″ to ¾″ in diameter ordinarily being preferred. Especially preferred silica particles are sized at about 14 to 20 U.S. mesh (i.e., 0.0555 in. to 0.0331 in.) and have an apparent bulk density of about 0.2 to about 0.6 g/cc and a surface area of about 250 to about 500 m$^2$/g.

The metallic components of the catalyst may be incorporated therein according to any of the preparation procedures taught in the prior art. For example, these metal compounds may be incorporated into the silica carrier material during its preparation by admixing suitable silica soluble salts of the metallic components with same such as hydroxides, carbonates, nitrates, halides, and the like materials. The preferred procedure on the other hand involves impregnation of the preformed silica carrier material with suitable salts of the metallic components according to procedures well known to those of skill in the art. Best results are ordinarily obtained with an aqueous impregnation procedure using water-soluble salts of cobalt, chromium, aluminum and magnesium that do not adversely affect the silica carrier material, are economical and widely available, and are thermally decomposed to the corresponding metallic oxide at reasonable calcination conditions. The order of impregnation of the metallic component is not critical and they can be added to the silica carrier material in any convenient manner. I have found best results when the metallic ingredients are coimpregnated into the silica carrier material using an aqueous impregnation solution containing water-soluble salts of the metallic ingredients which decomposed to yield the corresponding metallic oxide at conventional calcination conditions. Suitable metallic salts useful in this impregnation procedure are the corresponding hydroxides, carbonates, nitrates, halides (particularly the chlorides) and the like water-soluble, decomposible metallic salts. Best results are ordinarily obtained with the corresponding metal nitrate salt. The most important parameter controlling the performance of my catalytic composite is the relative molecular ratios of these metallic ingredients; specifically, I have found good results with composites containing amounts of cobalt oxide, chromium oxide, alumina and magnesium oxide sufficient to result in (1) a mole ratio of chromium oxide to cobalt oxide of about 0.2:1 to about 2:1 (most preferably about 1:1 to about 1.75:1), (2) a mole ratio of alumina to cobalt oxide of about 0.05:1 to about 0.5:1 (most preferably about 0.1:1 to about 0.2:1) and (3) a mole ratio of magnesium oxide to cobalt oxide of about 0.05:1 to about 0.5:1 (especially about 0.2:1 to about 0.4:1). Another performance parameter for these catalytic composites is the total metal oxide content; my findings indicate satisfactory results with a total metal oxide content of about 5 to about 75 wt. % of the total composite, with best results obtained at about 20 to about 30 wt. % of the composite.

In a highly preferred embodiment, the catalytic composite used in the present invention is a combination of about 12.1 wt. % cobalt oxide, about 11.5 wt. % chromium oxide, about 0.8 wt. % alumina and about 0.6 wt. % magnesium oxide with about 75 wt. % silica gel particles having a U.S. mesh size of about 14 to 20, and a surface area of about 340 m$^2$/g, prepared by impregnating the silica gel particles with an aqueous impregnation solution containing the necessary amounts of cobalt nitrate, chromium nitrate, magnesium nitrate and aluminum nitrate selected to result in the specified wt. % quantities of metallic oxides after calcination at about 500° to about 800° C. (preferably about 600° C.) for one to ten hours in an oxygen containing atmosphere such as a flowing stream of air. For this particular composite, the ratio of chromium oxide to cobalt oxide is 1.5:1, the ratio of alumina to cobalt oxide is 0.15:1 and the ratio of magnesium oxide to cobalt oxide is 0.3:1.

The oxygen reactant utilized in the method of the present invention may be substantially pure oxygen, air, or a mixture of oxygen with an inert gas such as nitrogen or a noble gas. It may also be introduced into the hydrocarbon input stream as a decomposable feed additive such as hydrogen peroxide which liberates oxygen in the required quantities under the conditions prevailing in the oxydehydrogenation reactor. The oxygen reactant may be added to the instant method in various ways such as it can be admixed with relatively cool input hydrocarbon stream or with the steam diluent or it may be added directly to the reactor independently of the input hydrocarbon stream or the steam diluent. In addition, the oxygen reactant can be added at one or more points in the reactor in such a fashion as to minimize local concentrations of oxygen relative to hydrogen and to smooth out the exothermic reaction of produced hydrogen with the oxygen reactant over the entire length of the reaction zone. In fact, multiple injection points for the oxygen reactant in the oxydehydrogenation reactor is a preferred mode of operation for the instant method. This procedure minimizes the opportunity for local build-up of the concentration of oxygen relative to the amount of hydrogen available for reaction therewith, thereby minimizing the opportunity for undesired reaction of oxygen with either feed or product hydrocarbon. The amount of oxygen charge should be sufficient to provide a mole ratio of oxygen to input dehydrogenatable alkylaromatic hydrocarbon of about 0.5:1 to about 2:1 and more preferably 0.75:1 to about 1.25:1. Since in the ideal case where each mole of feed hydrocarbon that is dehydrogenated yields one mole of hydrogen, it is obviously a preferred mode of operation to add, after an appropriate allowance for reaction inefficiency, only sufficient oxygen to consume the expected production of hydrogen at the particular oxydehydrogenation condition selected. Put another way, the optimum amount of oxygen is that just sufficient to consume the hydrogen produced by the primary dehydrogenation reaction without chewing up available feed or product hydrocarbon by an undesired hydrocarbon combustion reaction.

The quantity of steam used in the instant method may vary widely within a range of about 5:1 to about 25:1 moles of steam per mole of feed hydrocarbon and preferably, about 8:1 to about 12:1 moles of steam per mole of input hydrocarbon. The steam diluent may be introduced into the oxydehydrogenation reaction zone in the various ways known to those who are skilled in the art. It may be admixed directly with the relatively cool input hydrocarbon stream or it may be added directly to the reactor at a number of points spaced along the path that the reactants flow through during their passage through the reaction zone. The preferred mode of operation is ordinarily to split the input steam diluent stream into a number of portions, add a first portion to the feed hydrocarbon in order to raise the temperature thereof, with the other portions being injected into the oxydehydrogenation reaction zone at one or more points along the flow path of the reactants therethrough in order to provide intermediate heating of the reacting mixture. It is a feature of the present invention that superheated steam is not required for optimum utilization of the instant novel activated catalytic composite when it is used in oxydehydrogenation service.

According to the method of the present invention, a mixture of the dehydrogenatable alkylaromatic hydrocarbon, steam and oxygen is contacted with the novel multimetallic catalytic composite of the present invention in an oxydehydrogenation zone maintained at oxydehydrogenation conditions. This contacting step may be accomplished by using the catalyst in a fixed bed system, a moving bed system, a fluidized bed system, or in a batch type operation. However, in view of the well-known operational advantages associated with a fixed bed operation, it is preferred to use one or more reaction zones containing fixed catalyst beds in the present method. In this system, the input hydrocarbon feedstream is admixed with the required quantity of steam to achieve the desired inlet reactor temperature and with the desired quantity of oxygen and the resulting mixture is then passed into an oxydehydrogenation zone containing one or more fixed beds of the present catalyst. It is of course understood that the oxydehydrogenation zone may be one or more separate reactors with suitable means for injecting additional steam therebetween to inusre that the desired conversion temperature is maintained at the entrance to each reactor. It is also to be noted that the reactants may be contacted with the catalyst bed in either upward, downward or radial flow fashion, with the latter being preferred. In addition, it is to be noted that best results are obtained when the present method is conducted with all of the reactants present in the vapor phase in the oxydehydrogenation reaction zone.

The oxydehydrogenation conditions utilized in the process of the present invention include: (1) an inlet reactor temperature of about 470° to about 600° C. and more preferably about 470° C. to about 550° C., (2) a liquid hourly space velocity (LHSV), based on hydrocarbon feed, of about 0.5 to about 10 hours$^{-1}$, with a preferred value being about 0.75 to about 2 hrs.$^{-1}$, (3) a reactor pressure of about atmospheric or slightly above depending on the pressure drop through the reactor train; that is, a reactor pressure of about 1 to about 3 atmospheres, with the preferred value being an inlet pressure sufficient to overcome the pressure drop through the reactor train and to ensure adequate residence time for the input hydrocarbon in the reaction zone and which results in an effluent reactor pressure of approximately atmospheric pressure. It is to be noted that the specific values of oxydehydrogenation conditions are selected from the ranges stated as a function of the specific nature of the inlet dehydrogenatable alkylaromatic compound with a more severe set of conditions being selected for the more refractory inlet hydrocarbons such as ethylbenzene and less severe conditions being selected for the more easily dehydrogenated hydrocarbons. It is to be noted that the stated values of liquid hourly space velocity are calculated on the basis of liquid volume amount of inlet hydrocarbon charged to the oxydehydrogenation zone per hour divided by the volume of the instant catalytic composite utilized therein.

Regardless of the specific conditions utilized in the operation of the oxydehydrogenation step, an effluent stream will be withdrawn therefrom at a rate which will assure an adequate residence time for the desired reaction associated therewith and thereafter immediately quenched in order to obviate any possibility of inducing polymerization of the desired alkenylsubstituted aromatic hydrocarbons due to exposure to high temperatures for prolonged periods of time. The resulting quenched reaction effluent is subjected to fractional distillation in order to separate the product hydrocarbon from unreacted input hydrocarbon, dealkylated aromatic hydrocarbons and tars and polymers formed due to undesired polymerization side reactions. This separation step is ordinarily done by means of a vacuum distillation procedure in order to keep the fractionation temperatures at a reasonably low level whereat the degree of polymerization of the product alkenylaromatic hydrocarbon is minimized. Ordinarily an alkenylaromatic hydrocarbon polymerization inhibitor is added to this distillation step in order to further suppress undesired polymerization reactions. Typically, the inhibitor is sulfur or one of the dinitrophenols or an alkylcatechol such as t-butylcatechol (TBC). The desired alkenyl-substituted aromatic product hydrocarbon is separated as a bottom product in a distillation zone wherein the unreacted alkyl-substituted aromatic feed hydrocarbon is taken overhead. The resulting recovered unreacted input alkyl-substituted aromatic hydrocarbon is then recycled to the oxydehydrogenation reaction zone in order to furnish a portion of the hydrocarbon material fed thereto. The details associated with the distillation procedure used in this separation step are well known to those skilled in the art and will not be repeated here.

The following examples are presented to further illustrate the oxydehydrogenation method of the present invention and the novel multimetallic catalytic composite associated therewith. These examples are intended to be illustrative rather than restrictive.

EXAMPLE I

An aqueous impregnation solution containing cobalt nitrate, chromium nitrate, aluminum nitrate and magnesium nitrate was prepared and admixed with particles of a commercially available silica gel carrier material. The amounts of the metallic reagents contained in the impregnation solution were calculated to result in a final catalytic composite containing, on a metallic oxide basis, 12.1 wt. % cobalt oxide, 11.5 wt. % chromium oxide, 0.8 wt. % aluminum oxide, and 0.6 wt. % magnesium oxide. The silica carrier material was used in a 14 to 20 U.S. mesh size and it possessed a 0.4 g/cc apparent bulk density, a surface area of 340 $M^2/g$ and a pore volume of 1.15 cc/g. The impregnation step was performed by adding the silica carrier material particles to the impregnation solution with constant agitation. In addition, the volume of the impregnation solution was approximately the same as the bulk volume of the silica carrier material particles so that all of the particles were immersed in the impregnation solution. The impregnation solution was maintained in contact with the silica carrier material particles for a period of about one-half to about 3 hrs. at atmospheric pressure and at a temperature of about 70° F. Thereafter, the temperature of the impregnation mixture was raised to about 225° F. and the excess solution was evaporated in a period of about one hour. The resulting dried impregnation particles were then subjected to an oxidation or calcination treatment in a dry air stream at a temperature of about 1100° F., atmospheric pressure and a gas hourly space velocity of about 500 $hr.^{-1}$ for a period of about five hours. This oxidation step was designed to convert substantially all of the metallic ingredients in the catalytic composite to the corresponding metallic oxide form. The resulting catalytic composite constitutes a specific embodiment of the catalytic composite of the present invention and is hereinafter designated Catalyst A.

EXAMPLE II

In order to compare the novel activated multimetallic catalytic composite of the present invention with the various metallic oxide compositions suggested by the prior art in a manner calculated to bring out the beneficial interaction of the four metallic oxides hereinbefore specified for the composition of the present invention, a comparison test was made between the catalyst of the present invention prepared in accordance with Example I, Catalyst A, and three control catalysts, Catalyst $C_1$, $C_2$ and $C_3$. The first control catalyst, Catalyst $C_1$, was a combination of cobalt oxide and chromium oxide with a silica carrier material. The second control catalyst, Catalyst $C_2$, was a combination of cobalt oxide, chromium oxide and magnesium oxide with a silica carrier material. The last control catalyst, Catalyst $C_3$, was a combination of specified amounts of cobalt oxide, chromium oxide and alumina with a silica carrier material. All of these control catalysts were prepared according to the methods specified in Example I with the exception that the mixture of metallic salts used in the impregnation solution was adjusted to account for the differences in composition. For all of these control catalysts, the silica carrier material was identical to the silica carrier material used in the preparation of Catalyst A. The composition and relevant oxide mole ratios for Catalyst A and the three control catalysts are summarized in Table 1.

TABLE I

| | CATALYST COMPOSITION | | | | | | | |
|---|---|---|---|---|---|---|---|---|
| Catalyst Type | $Co_3O_4$, wt. % | $Cr_2O_3$, wt. % | $Al_2O_3$, wt. % | MgO, wt. % | Silica, wt. % | $Cr_2O_3/Co_3O_4$ | $Al_2O_3/Co_3O_4$ | $MgO/Co_3O_4$ |
| A | 12.1 | 11.5 | 0.8 | 0.6 | 75 | 1.5:1 | 0.15:1 | 0.3:1 |
| $C_1$ | 12.8 | 12.2 | — | — | 75 | 1.5:1 | — | — |
| $C_2$ | 12.5 | 11.9 | — | 0.6 | 75 | 1.5:1 | — | 0.3:1 |
| $C_3$ | 12.4 | 11.8 | 0.8 | — | 75 | 1.5:1 | 0.15:1 | — |

These catalysts were then separately subjected to a high stress accelerated oxydehydrogenation test designed to determine in a relatively short period of time their relative activity, product-selectivity and yield-selectivity in a process for oxydehydrogenating a high purity ethylbenzene feed stream to produce styrene.

Each test run consisted of a series of three evaluation periods of 16 hours, each of these periods comprising a 4 hour line-out period followed by a 12 hour test period during which the liquid and gas products from the reactor containing the catalyst undergoing evaluation were collected and analyzed by gas chromatography. The test runs for all of the catalysts undergoing evaluation were performed at identical conditions which comprised a liquid hourly space velocity, based on ethylbenzene, of 1 $hr.^{-1}$, atmospheric pressure, and inlet reactor temperatures of 450° C. for period 1, 475° C. for period 2 and 500° C. for period 3. The reactant mixture charged to the reactor containing the catalyst undergoing evaluation comprised ethylbenzene, oxygen, nitrogen and steam in amounts sufficient to result in the following mole ratios: oxygen to ethylbenzene of 1:1, nitrogen to ethylbenzene of 10.1:1 and steam to ethylbenzene of 10:1.

All test runs were performed in a pilot plant scale oxydehydrogenation plant comprising ½" inside diameter stainless steel reactor, a fixed bed of 30cc of catalyst maintained in the reactor between stainless steel screens, a reactor effluent condenser, and conventional heating means, pumping means, compressing means and the like small-scale pilot plant type of equipment. The flow scheme utilized in this plan involves forming a heated mixture of ethylbenzene, oxygen, nitrogen and steam in the quantities hereinbefore specified and passing same into the top of the reactor containing the catalyst undergoing evaluation as a stationary bed. The reactant mixture then passes downflow through the catalyst bed and an effluent stream is withdrawn from the bottom of the reaction zone, cooled in a water-cooled condenser to a temperature of about 10° to 25° C. and the resulting condensed effluent passed to a gas-liquid separating zone wherein a gas phase is allowed to separate from a liquid phase comprising an organic condensate phase containing styrene, benzene, toluene, and various tars and polymers and a water phase. The organic condensate was then analyzed by gas liquid chromatography procedures to determine the styrene, benzene and toluene content.

Figure 2:
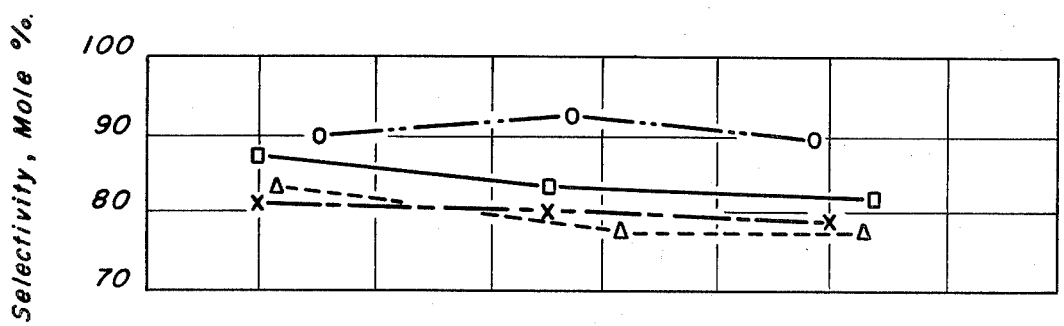
Figure 3:
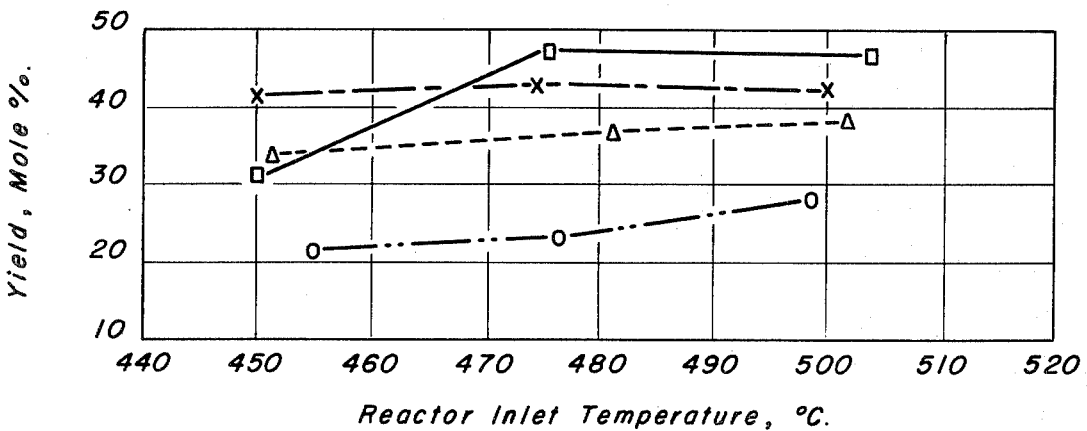

The results of the separate test performed on the catalyst of the present invention, Catalyst A, and the control Catalysts $C_1$, $C_2$ and $C_3$ are presented in FIGS. 1, 2 and 3 as a function of reactor inlet temperature measured in °C. FIG. 1 shows graphically the relationship between conversion expressed in mole percent of ethylbenzene charged as a function of reactor inlet temperature. FIG. 2, on the other hand, plots the observed product-selectivity for styrene production measured in terms of mole percent styrene produced per mole of converted feed ethylbenzene. And finally FIG. 3 tracks yield-selectivity for styrene production in percentage terms of moles of styrene produced per mole of ethylbenzene charged.

Referring now to the results of the comparison test run presented in FIGS. 1, 2 and 3 were Catalyst A, $C_1$, $C_2$ and $C_3$, it is immediately evident that the activated multimetallic catalytic composite of the present invention, Catalyst A, substantially outperforms the three control catalysts in activity as measured by conversion numbers given in FIG. 1 at a reactor inlet temperature above about 470° C. FIG. 2 is somewhat difficult to interpret because it plots product selectivity and it appears to indicate superior results for Catalyst $C_2$ which is the magnesium oxide attenuated cobalt oxide plus chromium oxide catalyst system. However, the data presented in FIG. 2 has to be weighed against the very poor performance of Catalyst $C_2$ in the activity numbers presented in FIG. 1. Put another way, the apparent superior performance for product selectivity for Catalyst $C_2$ in FIG. 2 is somewhat deceptive because of its very poor activity performance numbers presented in FIG. 1. When the apparent superiority of the data for Catalyst $C_2$ is properly discounted by its activity characteristics, it is clear from FIG. 2 that Catalyst A exhibited superior product-selectivity characteristics at all temperature test conditions. Turning now to FIG. 3 which plots percentage yield of styrene per mole of ethylbenzene charged, it is immediately evident that above a temperature of about 470° C. Catalyst A exhibits significantly improved yield characteristics relative to the three control catalysts. The data presented in FIG. 3 immediately highlights the surprising and significant difference in yield-selectivity between the four catalyst systems evaluated. The unexpected results associated with the present invention are clearly evident if the effect of magnesium oxide on the cobalt oxide-chromium oxide system is studied by evaluating the results for the ternary metallic oxide system, Catalyst $C_2$, relative to the performance for the binary metallic oxide system, Catalyst $C_1$. This comparison shows that the effect of magnesium oxide on the binary metallic oxide system was to cause a substantial depression in activity as manifested by conversion in FIG. 1 with an improvement in product-selectivity as shown in FIG. 2 which, taken together, caused the catalyst system $C_2$ to show very poor performance for yield-selectivity as is clearly demonstrated in FIG. 3. In sharp contrast to this detrimental interaction, the beneficial interaction of magnesium oxide with the alumina-containing catalyst system of the present invention is clearly demonstrated by comparing the results for Catalyst $C_3$, the cobalt oxide-chromium oxide-alumina catalyst system, with those exhibited for the catalyst of the present invention which only differs from Catalyst $C_3$ by the incorporation of magnesium oxide. In contradistinction to the deactivating effect of magnesium oxide observed in the comparison between Catalysts $C_2$ and $C_1$, the comparison of the performance of Catalyst $C_3$ with Catalyst A indicates an unexpected and surprising increase in activity for Catalyst A above 470° C. coupled with a substantial increase in both product-selectivity and yield-selectivity.

In final analysis it is clear from the data presented in the attached figures that the use of a quaternary metallic oxide catalyst system as specified by the present invention provides an efficient and effective means for significantly promoting an oxydehydrogenation process.

It is intended to cover by the following claims all changes and modifications of the above disclosure of the present invention which would be self-evident to a man of ordinary skill in the alkylaromatic dehydrogenation art or in the oxydehydrogenation catalyst formulation art.

I claim as my invention:

1. A method for oxydehydrogenating an aromatic input hydrocarbon having at least one dehydrogenatable alkyl group substituent to produce an alkenyl-substituted aromatic product hydrocarbon which comprises contacting the input hydrocarbon, steam and oxygen at oxydehydrogenation conditions, including an inlet reactor temperature of about 470° C. to about 550° C., with a catalytic composite consisting essentially of a combination of cobalt oxide, chromium oxide, alumina and magnesium oxide with a silica carrier material in amounts sufficient to result in a mole ratio of chromium oxide to cobalt oxide of about 0.2:1 to about 2:1, of alumina to cobalt oxide of about 0.05:1 to about 0.5:1 and of magnesium oxide to cobalt oxide of about 0.05:1 to about 0.5:1.

2. A method as defined in claim 1 wherein the total metal oxide content of said composite is about 5 to about 75 wt. % of the composite.

3. A method as defined in claim 1 wherein the ratio of chromium oxide to cobalt oxide in said composite is fixed at about 1:1 to about 1.75:1, the ratio of alumina to cobalt oxide is set at about 0.1:1 to about 0.2:1 and the ratio of magnesium oxide to cobalt oxide corresponds to about 0.2:1 to about 0.4:1.

4. A method as defined in claim 1 wherein the total metal oxide content of said composite is about 20 to about 30 wt. % of the composite.

5. A method as defined in claim 1 wherein the mole ratio of oxygen to input hydrocarbon is about 0.5:1 to about 2:1.

6. A method as defined in claim 1 wherein the mole ratio of steam to input hydrocarbon is about 5:1 to about 25:1.

7. A method as defined in claim 1 wherein the oxydehydrogenation conditions utilized include a temperature of about 470° C. to about 550° C., a pressure of about 1 to 3 atmospheres, and a liquid hourly space velocity of about 0.5 to about 10 $hr.^{-1}$.

8. A method as defined in claim 1 wherein the input hydrocarbon is ethylbenzene and the product hydrocarbon is styrene.

9. A method as defined in claim 1 wherein the input hydrocarbon is isopropylbenzene and the product hydrocarbon is alpha-methylstyrene.

* * * * *